(12) United States Patent
Grolla et al.

(10) Patent No.: US 9,116,089 B2
(45) Date of Patent: Aug. 25, 2015

(54) DEVICE FOR FILTERING BLOOD

(75) Inventors: Marc Grolla, Gelsenkirchen (DE); Gert Blankenstein, Cambridge, MA (US); Dirk Osterloh, Unna (DE)

(73) Assignee: Boehringer Ingelheim Microparts GmbH, Ingelheim am Rhein (DE)

( * ) Notice: Subject to any disclaimer, the term of this patent is extended or adjusted under 35 U.S.C. 154(b) by 0 days.

(21) Appl. No.: 13/883,909

(22) PCT Filed: Nov. 3, 2011

(86) PCT No.: PCT/EP2011/069350
§ 371 (c)(1),
(2), (4) Date: Aug. 14, 2013

(87) PCT Pub. No.: WO2012/062651
PCT Pub. Date: May 18, 2012

(65) Prior Publication Data
US 2013/0341265 A1 Dec. 26, 2013

(30) Foreign Application Priority Data
Nov. 10, 2010 (EP) .................................. 10014437

(51) Int. Cl.
*G01N 1/34* (2006.01)
*B01L 3/00* (2006.01)
*G01N 33/49* (2006.01)
*G01N 33/52* (2006.01)
*G01N 33/543* (2006.01)

(52) U.S. Cl.
CPC ............... *G01N 1/34* (2013.01); *B01L 3/5023* (2013.01); *B01L 3/50273* (2013.01); *G01N 33/491* (2013.01); *B01L 2200/0621* (2013.01); *B01L 2200/0684* (2013.01); *B01L 2300/0681* (2013.01); *B01L 2300/0825* (2013.01); *B01L 2300/0864* (2013.01); *B01L 2400/049* (2013.01); *B01L 2400/0481* (2013.01); *B01L 2400/0487* (2013.01); *B01L 2400/0694* (2013.01); *G01N 33/521* (2013.01); *G01N 33/54366* (2013.01)

(58) Field of Classification Search
USPC ....................................................... 210/416.1
See application file for complete search history.

(56) References Cited

U.S. PATENT DOCUMENTS

| 7,005,109 | B2 | 2/2006 | Husar | |
| 8,333,712 | B2 * | 12/2012 | Imamura et al. | 600/583 |
| 2002/0061260 | A1 * | 5/2002 | Husar | 422/100 |
| 2002/0098114 | A1 * | 7/2002 | Harding et al. | 422/56 |
| 2006/0018790 | A1 * | 1/2006 | Naka et al. | 422/58 |

(Continued)

FOREIGN PATENT DOCUMENTS

| DE | 19933458 A1 | 2/2001 |
| EP | 0992287 A2 | 4/2000 |

(Continued)

OTHER PUBLICATIONS

International Search Report and Written Opinion for PCT Application PCT/EP2011/069350, dated Jan. 26, 2012.

*Primary Examiner* — Jennifer Wecker
(74) *Attorney, Agent, or Firm* — Michael P. Morris; Mary-Ellen M. Devlin

(57) ABSTRACT

A device is proposed having a separating device for filtering a liquid sample and having a conveying device. A positive pressure or negative pressure can be generated by means of the conveying device, for accelerating or assisting the filtration.

12 Claims, 3 Drawing Sheets

(56) References Cited

U.S. PATENT DOCUMENTS

2006/0228811 A1* 10/2006 Bedingham et al. .......... 436/174
2008/0050830 A1* 2/2008 Floriano et al. ................ 436/63
2008/0118399 A1* 5/2008 Fleming ....................... 422/68.1
2008/0128341 A1* 6/2008 Jang et al. ..................... 210/137
2009/0130766 A1* 5/2009 Weekamp ....................... 436/63

2013/0341265 A1 12/2013 Grolla

FOREIGN PATENT DOCUMENTS

WO 03057369 A1 7/2003
WO 2012062651 A1 5/2012

* cited by examiner

DEVICE FOR FILTERING BLOOD

The present invention relates to a device for the manipulation, particularly the filtration, of a liquid sample, particularly blood, according to the preamble of claim 1 or 5.

The present invention relates to the manipulation or filtration of a liquid sample. This may be in particular a biological sample or sample liquid, particularly blood or the like. In particular, the present invention relates to the filtration of a particle-containing solution (suspension) such as blood or another human or animal bodily fluid.

The present invention relates in particular to fluidic devices which contain or form a microfluidic system. The remarks that follow therefore preferably relate to devices in which capillary forces act and are in particular important or crucial to the operation.

Devices are known in which blood is filtered by means of a flat separating device (membrane). The filtrate or permeate is received in a chamber flatly adjoining the separating device and is discharged laterally through a channel. Devices of this kind for blood separation are known for example from WO 2005/119211 A1 and WO 2009/106331 A2.

The blood separation can be accelerated by the exertion of a pressure, particularly by the application of negative pressure. This is disclosed inter alia in EP 1 421 993 A1, which constitutes the closest prior art. EP 1 421 993 A1 discloses a device for blood separation, in which a support comprising a nonwoven carrier material, e.g. made of glass fibres, is provided with a nonwoven separating material in a blood separation area. The nonwoven separating material forms a filter or a separating device for separating off blood constituents. The blood separation is carried out by capillary forces, while a negative pressure may be applied in an assisting capacity. However, no technical means of producing the negative pressure are disclosed. After the blood separation, the separated blood plasma is removed from the nonwoven carrier material by squeezing it out. If necessary, the region of the support comprising the nonwoven carrier material can be separated from the remainder of the support, so as to prevent potential contamination of the blood plasma by blood cells. A disadvantage here is that there is a relatively irregular and slow separation of the blood and conveying of the separated blood plasma into a nonwoven material. A further disadvantage is that a separate squeezing device is needed to remove the separated blood plasma.

The problem of the present invention is to provide a device for the manipulation, particularly the filtration, of a liquid sample such as blood, while enabling optimised or defined manipulation, particularly filtration, a compact structure for the apparatus as a whole and/or a defined or easy discharge of the sample that has been manipulated or filtered.

The above problem is solved by a device according to claim 1 or 5. Further features are the subject of the sub-claims.

In one aspect, the invention relates to providing the device with a conveying device for producing negative and/or positive pressure for conveying the sample. This allows defined or rapid manipulation, particularly filtration, of the sample. The conveying device is preferably arranged on or formed by a support, forming a fluidic system for the sample. This allows the construction to be very simple and/or compact.

Preferably, the device comprises a separating device for the sample, the separating device being arranged on a first region of the support. The conveying device is preferably arranged separately therefrom or in a second region of the support, the two regions preferably being adapted to be separated from one another. This second region of the support preferably also comprises a reservoir for the manipulated or filtered sample.

By the removal of the first support region with the separating device it is possible to achieve simple and space-saving storage of the sample held in the second support region. Alternatively or additionally, this facilitates the discharging of the sample held in the second support region, in particular by means of the conveying device Preferably, the conveying device is embodied both to generate a negative pressure, particularly in order to bring about, accelerate or assist filtration, and to generate a positive pressure, particularly for the discharging of the filtered sample. Thus, the conveying device can preferably be used both to hold the sample and to discharge the sample and thus has a dual function, in particular. This aspect of the present invention can also be implemented independently of the separability of the first support region or with the separating device.

Another aspect of the present invention, which can also be implemented independently is directed to the fact that the conveying device comprises a deformation region of a cover of the support with the fluidic system for the sample, the deformation region being flexibly deformable in order to produce a negative and/or positive pressure and/or in order to convey the sample. This allows the construction to be made very simple and/or compact. Moreover, very simple actuation is made possible, for example by the operator's finger or fingertip or the like.

Particularly preferably, the deformation region, like the rest of the cover of the support, is formed by a film which in particular covers recesses, channels or the like formed in the support to form the fluidic system. This allows a very simple and compact construction.

The support preferably comprises a flat or dish-shaped depression or recess to allow the deformation region to be deformed into the support. The depression or recess is preferably connected to the fluidic system or sample via a channel or the like.

Alternatively, the cover or the deformation region may also be embodied separately from the rest of the cover, and/or as a plug, and/or may comprise or form a ram. The cover or the deformation region in turn covers a preferably cylindrical depression or recess in the support and in order to produce a negative or positive pressure in the recess, is movable into it and/or out of it, particularly preferably at right angles to the flat extent of the support or cover, for example by means of a preferably moulded-on actuating element such as a tab, eyelet or the like. This also provides a simple construction. Moreover, very simple actuation of the conveying device can be carried out or achieved, particularly by means of a manipulating device or the like, particularly preferably in automatic or self-actuating manner.

Further advantages, features, properties and aspects of the present invention will become apparent from the claims and the description of preferred embodiments that follow, with reference to the drawings, wherein:

In the figures, the same reference numerals have been used for identical or similar parts, where corresponding or comparable properties and advantages are obtained, even if the associated description has not been repeated.

Figure 1A:
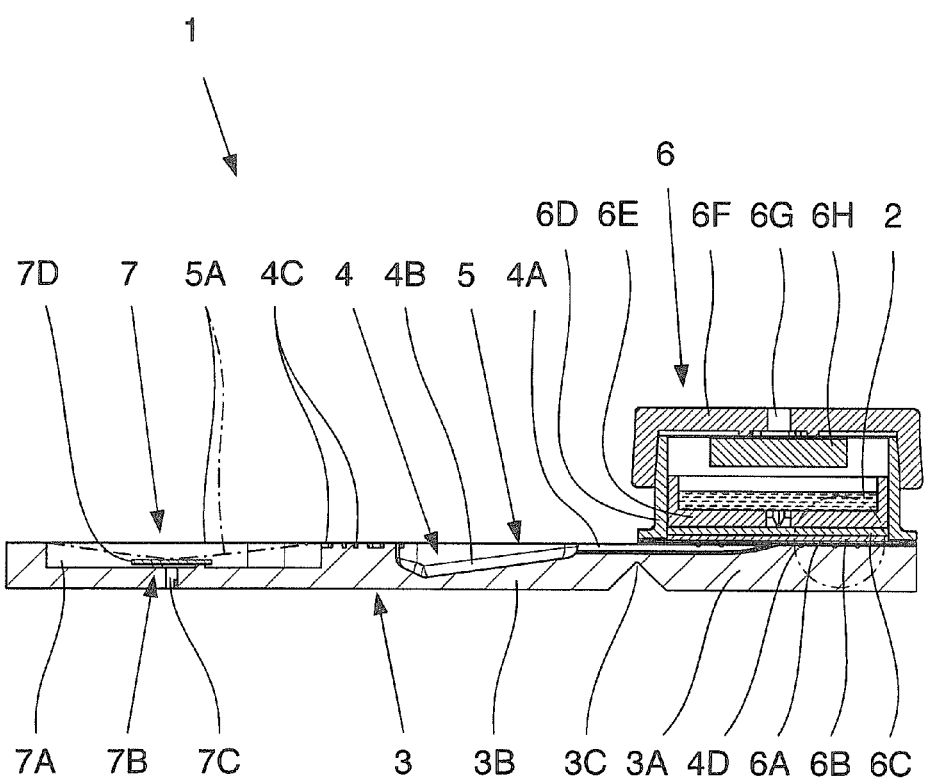
FIG. 1A is a schematic section through a proposed device, according to a first

FIG. 1A shows, in schematic section, a proposed device 1 for the manipulation and particularly filtration of a liquid sample 2. In particular, the sample 2 is a particle-containing solution or suspension. Particularly preferably, it is a biological sample 2.

In the embodiment shown, it is, in particular, blood or some other human or animal bodily fluid. However, other liquids or suspensions or the like may also be manipulated or filtered as the sample 2.

Although the device 1 is particularly preferably used for filtration of the sample 2, this is not obligatory. Rather, any other manipulation may be carried out alternatively or additionally, such as mixing with a reagent, a solvent or the like, or other treatment or investigation of the sample 2.

Figure 2:
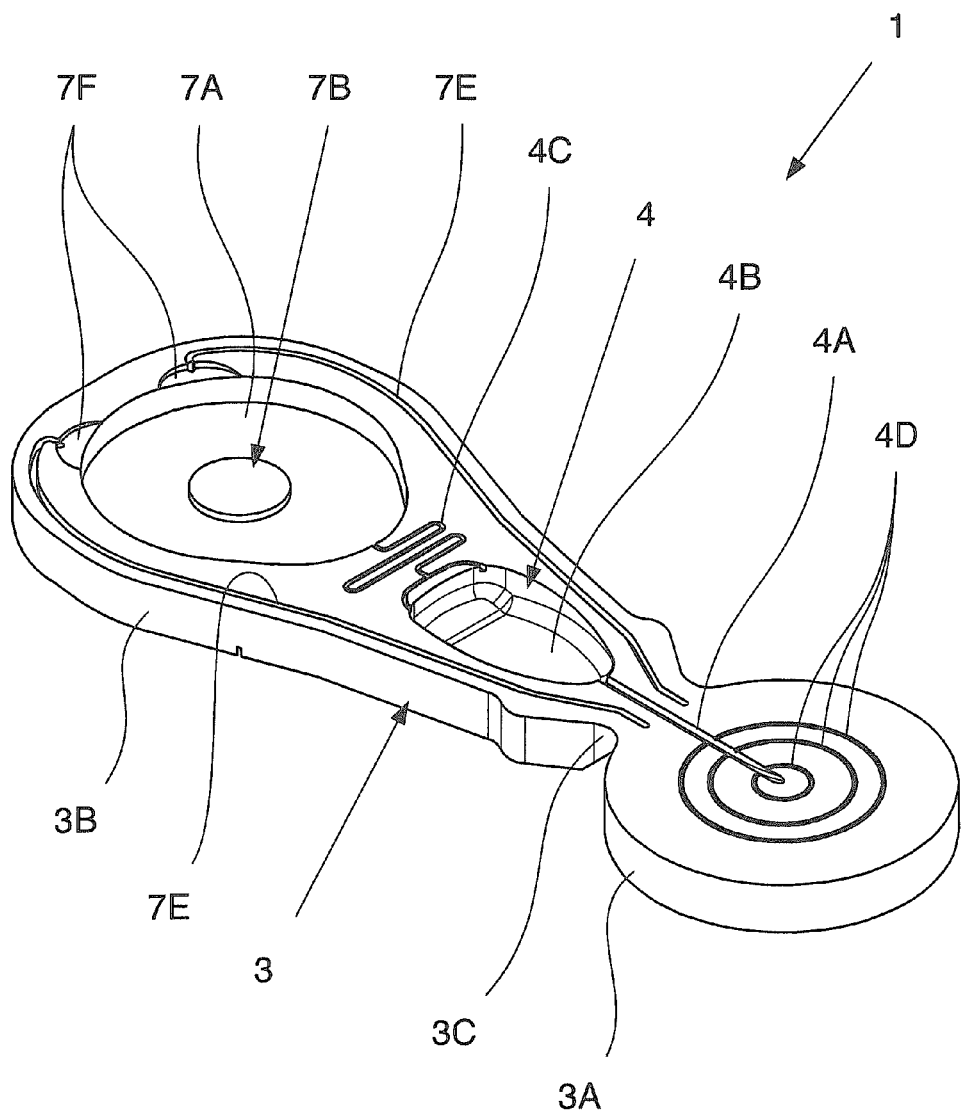
FIG. 2 is a perspective view of a support of the proposed device according to the first embodiment.

The device 1 comprises a support 3 which forms or comprises a fluidic system 4. In particular, the fluidic system 4 is at least partly or wholly formed by or in the support 4, optionally together with a cover 5. FIG. 2 shows the support 3 in a schematic perspective view.

The device 1 preferably comprises a cover 5 associated with the support 3, which preferably at least partly covers the fluidic system 4. In particular, the cover 5 covers depressions, grooves or the like formed in the support 3, preferably in fluidtight and more particularly in gastight manner as well—which form at least parts of the fluidic system 4.

The cover 5 is preferably at least substantially smooth, flat, elastically deformable and/or film-like in configuration. In particular, it is a plastics film or the like.

The cover 5 is preferably arranged or applied to a flat side of the support 3, for example by adhesion, sealing, particularly heat-sealing, welding or the like.

In the embodiment shown the device 1 or the support 3 or the fluidic system 4 preferably comprises a receiving channel 4A for the preferably filtered sample 2 or the permeate, a reservoir 4B attached thereto for preferably temporarily holding the preferably filtered sample 2 or permeate and/or a connecting channel 4C, as shown in the perspective view according to FIG. 2.

The device 1 preferably comprises a separating device 6 as shown in FIG. 1A for filtering the sample 2 or separating constituents or particles from the sample 2. The separating device 6 is preferably arranged on the support 3, particularly in a first support region 3A, and/or fixedly connected thereto.

The separating device 6 preferably comprises a flat filter element 6A, for example a membrane or the like, as a main filter for separating constituents such as particles, cells or the like from the sample 2. For example, the filter element may be formed by or provided with a membrane as described in WO 2009/106331 A2.

Figure 1B:
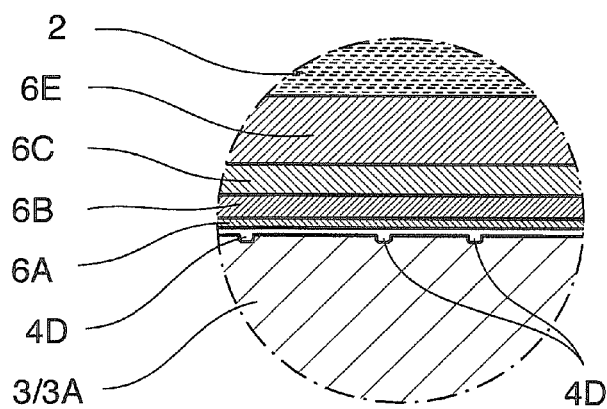
FIG. 1B is a magnified detail from FIG. 1A.

The separating device 6 or filtration is preferably of a multi-stage or multi-layer construction, in the embodiment shown. This is illustrated in more detail in FIG. 1B, which shows a magnification of FIG. 1A in the region of the separating device 6. In particular, the separating device 6 comprises another flat filter element 6B as a (first) preliminary filter and optionally also an additional, preferably flat filter element 6C as a second preliminary filter. The filter elements 6A, 6B and 6C are preferably layered directly above one another or placed with their flat sides against one another.

The main filter and the optional preliminary filters or the filter elements 6A, 6B and 6C are preferably housed in a housing 6D of the separating device 6. The housing 6D is preferably fixed to the support 3 or its support region 3A, particularly by adhesion, heat-sealing, welding or the like. The cover 5 preferably does not extend below the filter or the filter elements 6A, 6B, 6C, but may optionally extend somewhat underneath the housing 6D.

In the embodiment shown, the separating device 6 or its filter is additionally placed on the support 3. However, the separating device 6 or its filters may if desired also be integrated in the support 3, particularly held in a corresponding recess or depression in the support 3.

The main filter and the optional preliminary filters or the filter elements 6A, 6B and 6C are preferably held by an optional depressing means 6E flat, particularly on or against the support 3 or its facing surface. The depressing means 6E acts on the flat side of the filter elements 6A, 6B and 6C remote from the support 3, in particular on the outer filter element 6C in this case, i.e. on the receiving side of the filter, in particular in the manner of a lattice, ribs or spokes or lies on the flat side of the filter, in this case of the outer filter element 6C, such that the sample 2 can be evenly distributed over the filter (in this case the filter element 6C) and/or can penetrate into it easily or over a wide area. The depressing means 6E is for example held in the housing 6D by clamping or by some other suitable means. However, other design solutions are also possible for suitably forming, tensioning, holding and/or securing the filter or filter elements 6A, 6B and 6C.

As a result of the above-mentioned construction of the depressing means 6E or another suitable construction, the sample 2, for example a drop of blood, which has already been received, according to FIG. 11, is able to be uniformly distributed over the filter or the upper filter element 6C and to penetrate into the filter or, in this case, the filter elements 6C, 6B and 6A one after the other.

The separating device 6 or the housing 6D or the sample receptacle formed thereby can preferably be covered by a cover 6F. FIG. 1 shows the device 1 or separating device 6 with the cover 6F placed thereon. The separating device 6 or the housing 6D is preferably provided with a vent which is formed here by a vent opening 6G, for example in the cover 6F. The vent prevents any negative pressure occurring on the receiving side of the filter in the separating device 6, particularly when the sample 2 penetrates into the filter or support 3 or the fluidic system 4, as a negative pressure of this kind would counteract the desired rapid or easy filtration.

In order to be able to prevent the sample 2 escaping through the vent opening 6G, a stop element 6H, for example a membrane, a cover or the like, may be associated with the vent opening 6G, as indicated in FIG. 1.

The fineness of the filter elements 6A, 6B and 6C or the pore size preferably increases or decreases, respectively, towards the support 3. In particular, the main filter or the filter element 6A filters the smallest particles, cells, or the like, that are to be separated off, from the sample 2.

The sample 2 is preferably (also) taken up in the filter and/or filtered or passed through the filter by capillary forces.

The filtered sample 2 or the permeate is taken up by the support 3 or the fluidic system 4, particularly the receiving channel 4A which extends to a point underneath the separating device 6 or the filter, and discharged. To assist with this uptake, the support 3 is preferably provided with a suitable structure, additional discharge channels 4D, which extend in an annular configuration in this case, for example, as shown in FIG. 2.

The uptake of the (filtered) sample 2 into the fluidic system 4 or the receiving channel 4A and the reservoir 4B is preferably (also) carried out by capillary forces.

The filtered sample 2 then flows through the receiving channel 4A into the reservoir 4B. However, the filtered sample 2 may also be conveyed to another investigation region, treatment region or the like.

The device 1 comprises a conveying device 7 for producing a negative and/or positive pressure or for conveying the sample 2.

The conveying device 7 serves in particular to effect, accelerate or assist the manipulation of the sample 2, particularly its filtration, and/or the later delivery of the filtered sample 2, in this case from the reservoir 4B. Particularly preferably, the conveying device 7 assists the capillary forces acting during the filtration and the uptake of the (filtered) sample 2 into the fluidic system 4, so that in general the manipulation and in particular the filtration and uptake of the sample 2 is assisted. However, the conveying device 7 or the negative and/or positive pressure generated by it can also decisively or exclusively bring about the manipulation of the sample 2, particularly the filtration and/or uptake of the sample 2.

In the embodiment shown, the conveying device 7 comprises a deformation region 5A which is formed by or embodied in one piece with the cover 5, in particular. The deformation region 5A is arranged above a depression or recess 7A which is formed in the support 3, in particular, in the embodiment shown. The conveying device 7 or depression 7A is preferably connected to the fluidic system 4 or the reservoir 4B by the connecting channel 4C.

In the undeformed state, or initial state, the deformation region 5A spans the depression 7A in the embodiment shown, preferably in at least substantially flat and/or planar manner. The deformation region 5A is preferably deformable, particularly in order to generate negative and/or positive pressure and/or to convey the sample 2. Particularly preferably, the deformation region 5A is elastically deformable and after deformation strives to return to its initial position by elastic restoring forces. The cover 5 is preferably formed from an elastically deformable foil or the like. Moreover, the cover 5 or the deformation region 5A may also be pre-tensioned.

To actuate the conveying device 7 or generate a negative or positive pressure, the deformation region 5 is deformed. This deformed state is shown by dashed lines in FIG. 1A. The actuation of the conveying device 7 or deformation of the deformation region 5A is preferably carried out manually, particularly with the thumb or another finger of a user (not shown), or in some other suitable manner.

The conveying device 7 preferably comprises a venting device 7B which, in the embodiment shown, comprises in particular a vent opening 7C, in this case in the base of the recess 7A or in the support 3, and an associated valve 7D for closing off the vent opening 7C. The venting device 7B or vent opening 7C prevents undesirable excess pressure from being generated in the recess 7A during the pressing in or deformation of the deformation region 5A into the recess 7A (the state of deformation into the recess 7A is shown by dashed lines in FIG. 1), as an excess pressure of this kind would counteract the desired direction of flow of the sample 2 through the separating device 6 into the fluidic system 4, particularly into the reservoir 4B. Instead, displaced air can escape through the venting device 7B or vent opening 7C.

In the embodiment shown, the venting device 7B or the valve 7D is closed, particularly by the deformation of the deformation region 5A or manually, particularly at the end of the deformation or the pressing of the deformation region 5A into the recess 7A. In the embodiment shown, this is done in particular by the abutting of the deformation region 5A on the valve 7D, the valve 7D then being closed. This is carried out in this case by the pressure applied to deform the deformation region 5A, particularly by a user (not shown), for example with the thumb or another finger, or by some other object such as a tool or punch or the like.

Alternatively, it is also possible for the valve 7D to close automatically, for example when a negative pressure is produced in the recess 7A or air begins to flow from outside through the vent opening 7C into the recess 7A. In fact, this happens when the deformation region 5A begins to return to its original undeformed state, after the deformation, particularly as a result of elastic resilience.

The deformed or pressed-in deformation region 5A (this state is shown by dashed lines in FIG. 1) seeks to return to its undeformed starting position after being released or freed, particularly as a result of elastic resetting and/or under the effect of some other resilient or spring element (not shown). As a result, a negative pressure is produced in the recess 7A, as the valve 7D or the venting device 7B is or remains closed or closes.

Accordingly, the fluidic system 4 which is fluidically connected to the recess 7A, in this case via the connecting channel 4C, is placed under negative pressure. This negative pressure causes the sample 2 to be aspirated or sucked into the fluidic system 4 or the reservoir 4B. As a result, the sample 2 is sucked through the filter or the separating device 6 or the filtration is assisted and in particular accelerated substantially.

The volume of the conveying device 7 (volume of the recess 7A and/or the possible or expected deformation of the deformation region 5A) is preferably selected so as to be substantially greater, in particular at least 50% greater, preferably at least 80% greater, than the volume of the sample 2 which is to be taken up by the separating device 6, more precisely its filter, and by the fluidic system 4 or the reservoir 4B. For the configuration of the device 1, it may also be envisaged that the above-mentioned volume of the conveying device 7 (volume of air that is displaced from the recess 7A during pressing-in or deformation) is greater than the volume of the sample 2 that is to be taken up or the reservoir 4B, by at least a factor of 2, most preferably by a factor of 3 or more. In this way, it can be ensured that a relatively high negative pressure is ensured particularly towards the end of filtration, thus ensuring very rapid filtration overall. This preferably also applies in corresponding manner when the deformation region 5A is deformed outwards, for example, and thereby tensioned, so as to generate a negative pressure or, on resetting, a positive pressure. Moreover, this preferably also applies to any other manipulation of the sample 2, i.e. even if the sample 2 is not subjected to filtration but only to some other treatment in the device 1.

After the filtration, the sample 2 is taken up or aspirated into the reservoir 4B.

The reservoir 4B for the (filtered) sample 2 and the conveying device 7 are preferably mounted on the support 3 separately from the separating device 6 or in a second region 3B of the support 3.

Preferably, the separating device 6 on the one hand and the reservoir 4B with the (filtered) sample 2 contained therein and the conveying device 7 on the other hand or (after filtration has been carried out) the two regions 3A and 3B can be separated from one another. For this purpose, the device 1 or the support 3 preferably comprises a weakened breaking point 3C which may be formed for example by a corresponding tapering of the material, a groove, a channel or the like, as shown in FIG. 1.

The separation of the two regions 3A and 3B is carried out in particular at right-angles to the receiving channel 4A or between the separating device 6 and the reservoir 4B. The weakened breaking point 3C is therefore preferably arranged in this region.

Particularly preferably, the two regions 3A and 3B are separated by bending the support 3 or the two regions 3A and 3B relative to one another, in the embodiment shown particularly preferably about an axis that is transverse of the longitudinal extent of the support 3, transverse of the receiving channel 4A and/or in the flat plane of the support 3.

However, the separation of the two regions 3A and 3B may also be carried out for example by cutting, for example using scissors or another cutting device (not shown) or by some other method.

The separation of the two regions 3A and 3B in the embodiment shown particularly preferably causes the receiving channel 4A to open up, so that this can then be used as the delivery channel for the sample 2 that is held or stored in the reservoir 4B, or forms a discharge opening for the sample 2 or the device 1 or the support 3.

To prevent air from being sucked into the fluidic system or the receiving channel 4A as the result of any negative pressure still remaining in the conveying device 7 and/or to prevent the sample 2 from being drawn into the connecting channel 4C and optionally the recess 7A, when the two regions 3A and 3B are separated, the device 1 is preferably configured so that the conveying device 7 or its recess 7A is automatically or autonomously vented when the two regions 3A and 3B are separated. This is preferably achieved by the fact that at least one, and in the drawing two, venting channels 7E extend in the or support 3 (covered here by the cover 5) from the recess 7A into the separating region or into the region of the weakened breaking point 3C or, in particular, somewhat beyond it, so that when the two support regions 3A and 3B are separated, at least one venting channel 7E, preferably both venting channels 7E, are opened outwards or to the environment. Accordingly, after the separation of the two regions 3A and 3B or after the separation of the separating device 6, ambient air can flow into the recess 7A or into the conveying device 7 and equalise the negative pressure still prevailing. The deformation region 5A which is still deformed at the moment of separation of the two regions 3A and 3B, in particular, can also return virtually immediately into its (undeformed) initial position.

It should be noted that other design solutions for venting can also be implemented.

The separated support region 3B comprises the reservoir 4B with the (filtered) sample 2 held therein and the associated conveying device 7. This unit can then be stored in a relatively limited space and optionally also refrigerated or even frozen, if desired.

Later, or directly after the separation of the regions 3A and 3B, the sample 2 can be removed from or discharged from the reservoir 4B, preferably by means of the conveying device 7. In particular, the conveying device 7 is configured so that a positive pressure can be generated for expelling the sample 2 from the reservoir 4B, particularly for delivering it through the receiving channel 4A. For this purpose, the deformation region 5A can be deformed again, particularly pressed in. In the embodiment shown, the venting channels 7E have to be closed. This can be done for example as a result of the deformation region 5A being applied to the recess 7A during the manual pressing onto transitional regions 7F of the venting channels 7E, thereby closing this recess 7A. However, other design solutions are also possible.

It should be noted that closing of aerating and/or vent openings or channels may optionally also be omitted, depending on the design of the structures or flow resistances, as for example relatively fast pressing-in can lead to a pressure increase in the recess 7A which may be sufficiently high to allow the sample 2 to be discharged from the reservoir 4B through the receiving channel 4A in the desired manner.

The removal of the filtered sample 2 from the reservoir 4B may alternatively also be carried out by piercing or perforating the cover 5 using a cannula or the like (not shown) or otherwise opening the fluidic system 4 or reservoir 4B and optionally aspirating the sample directly out of the reservoir 4B, in particular.

The connecting channel 4C is preferably selected to be long enough to prevent the sample 2 from penetrating into the recess 7A.

The reservoir 4B is preferably configured such that the sample 2 is held as compactly as possible in a region towards the receiving channel 4A in the reservoir 4B, particularly by means of corresponding capillary forces, and/or such that the sample 2 would only enter the connecting channel 4C if the reservoir 4B were completely full.

In the embodiment shown, the reservoir 4B is preferably of a ramp-like configuration—particularly for the reasons stated above—while the depth of the reservoir 4B preferably increases from the junction with the receiving channel 4A to the junction with the connecting channel 4C.

The support 3 is preferably of a flat and/or plate-like configuration. The support 3 is preferably at least substantially rigid in construction. The support 3 is preferably made of plastics, particularly by injection moulding. The channels, recesses, depressions and the like for forming the fluidic system 4 are preferably formed on the flat side of the support 3 which is covered (wholly or partially) by the cover 5.

The fluidic system 4 may also encompass the recess 7A, as the latter is connected thereto by the connecting channel 4C.

The device 1 and fluidic system 4 are, in particular, microfluidic arrangements. Microfluidic for the purposes of the present invention means that the individual volumes or total volumes are less than 5 ml, particularly less than 1 ml, most preferably less than 500 µl.

The present invention or device 1 envisages in particular the use of a vacuum or negative pressure as a drive mechanism for a filtration process. Alternatively, however, a positive pressure may also be used as a drive mechanism for the filtration process.

The present invention or device 1 envisages in particular the pressing in of an elastic cover 5 or film, preferably to create a positive pressure. The preferably elastic restoring force is used to produce a negative pressure. However, the deformation region or the film or cover 5 may also be pulled, particularly in order to produce a negative pressure.

A second embodiment of the proposed device 1 or the conveying device 7 will now be explained in more detail by reference to the schematic section in FIG. 3. Only essential differences from the first embodiment will be described, so that the previous remarks and explanations apply accordingly or in complementary fashion, in particular. Individual features of the different embodiments may in particular be combined with one another as desired, but also implemented independently of one another.

In the second embodiment, the conveying device 7 preferably comprises a ram 7G or a ram-like element or the like. In particular, the ram 7G is formed by a relatively rigid surface region or the like.

Particularly preferably, the ram 7G is formed by the deformation region 5A, which here covers the recess 7A or other cavity in the device 1 or support 3. Particularly preferably, the ram 7G or the deformation region 5A is movable into the recess 7A and/or within it and/or out of the recess 7A and/or outwards over the flat side or outside of the support 3 so as to generate a positive pressure and/or negative pressure or to convey the sample 2. In the second embodiment, the conveying device 7 or the cover 5, which is particularly preferably in the form of a plug, or the deformation region 5A thereof, comprises a fixing region 5B which is particularly preferably tightly secured to the support 3 or a flat side of the support 3 and for example surrounds the recess 7A in an annular or circumferential manner, and/or comprises a connecting region 5C which preferably connects the fixing region 5B to the ram 7G and/or is elastically deformable or invertible or comprises at least one bent or inverted deflecting region 5D. In particular, the invertible connecting region 5C or deflecting region 5D enables the ram 7G to move easily. However, other design solutions are also possible. In the second embodiment, the deformation region 5A or connecting region 5C is preferably embodied as a concertina-like or flexible tube, particularly to enable ease of deformation during the actuation or use of the conveying device 7. In the embodiment shown, an optionally pre-formed deflection through 180° takes place in the deflecting region 5D in at least one portion, in this case even in two portions of the deformation region 5A or connecting region 5C. However, other design solutions are also possible. The conveying device 7 or the deformation region 5A preferably comprises an actuating element 7H such as a tab, eyelet or the like. Particularly preferably, the actuating element 7H is moulded on in one piece.

In the second embodiment the conveying device 7 is actuated in particular by moving the actuating element 7H or the ram 7G into or out of the recess 7A. This may in turn be carried out manually or with the aid of a manipulating device of a drive, a motor or the like.

In the embodiments described hereinbefore, a movement or main deformation preferably takes place transversely, more particularly at least substantially perpendicularly with respect to the main plane of extent or flat side of the support 3. However, in principle, other directions of movement and/or arrangements are also possible.

The conveying device 7 or the cover 5 or the deformation region 5A in the embodiment shown is preferably formed in one piece and/or made of plastics, particularly by injection moulding. However, other design solutions are also possible.

Figure 3:
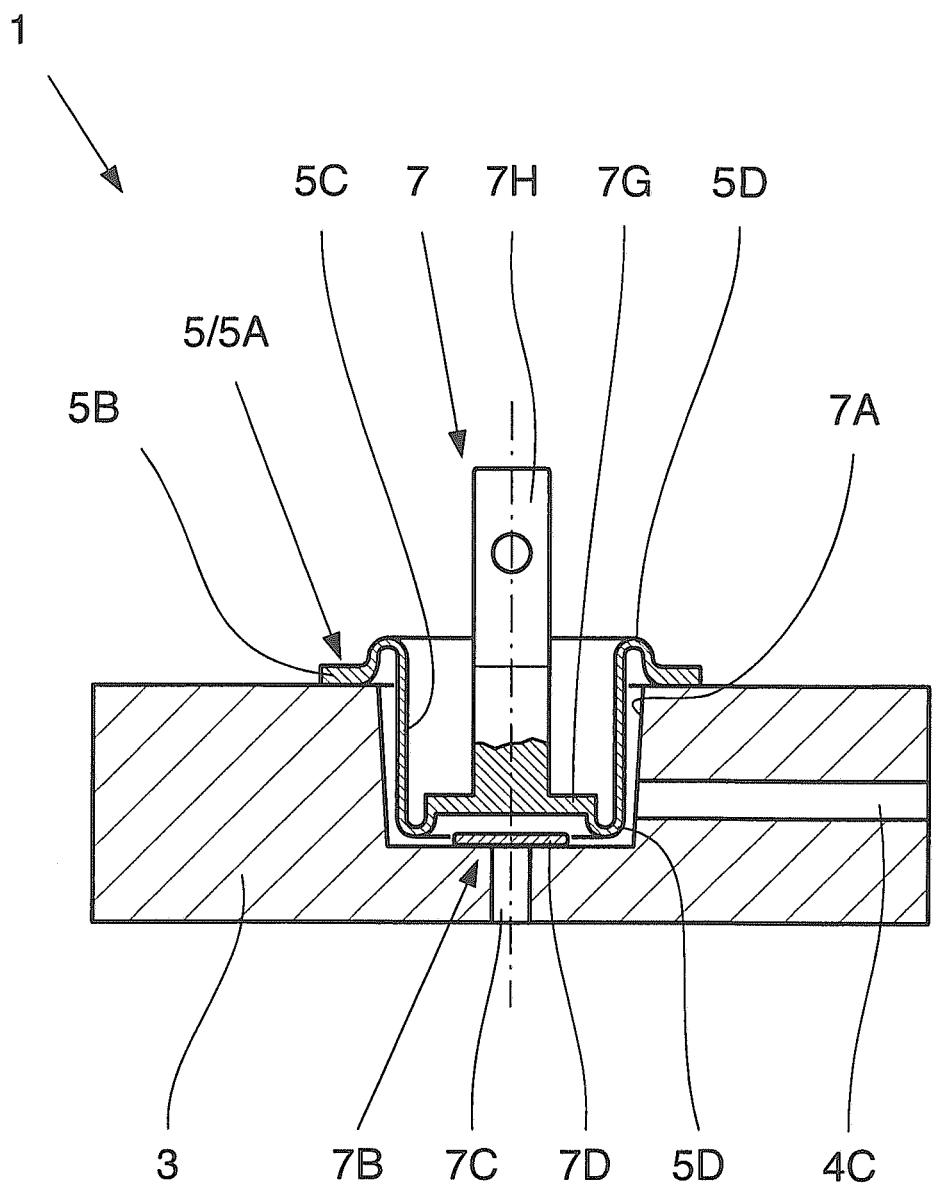
FIG. 3 is a schematic section through part of a proposed device according to a second embodiment.

The deformation region 5A is also preferably embodied, in the second embodiment, so as to assume a preferred starting position, for example the position shown in FIG. 3, in which the deformation region 5A or its ram 7G is located substantially in the recess 7 or in a pressed-in position. The deformation region 5A or ram 7G is then pulled out by means of the actuating element 7H and thereby preferably tensioned. Thus, particularly when the venting device 7B is closed or the valve 7D is closed, a negative pressure can be produced in the recess 7A, which can act, through the connecting channel 4C connected to the arrangement 7A, on the fluidic system 4 or on the sample 3 that is to be manipulated. After the actuating element 7H has been released or let go, the deformation region 5A or ram 7G can return to the starting position shown in FIG. 3, particularly as a result of elastic restoring forces, in order to produce a positive pressure, if required, in this case with the venting device 7B closed, in particular. However, this return to the starting position need not be brought about by elastic restoring forces but may theoretically also be assisted or exclusively brought about by an active restoring movement, for example by means of the actuating element 7H.

It should also be noted that restoring is not always necessary. Rather, if required, the conveying device 7 may also be embodied or used as a device for one-time actuation. In this case, for example, it is not necessary to carry out resetting. Rather, the deformation region 5A can remain in the deformed position after being deformed once.

It should also be noted that the valve 7D shown in the second embodiment in FIG. 3, or the venting device 7B shown therein, is purely optional. Depending on the construction or intended use, these may also be omitted.

The cover 5 or the deformation region 5A may if necessary also be embodied separately from any other cover of the support 3. In other words, the cover 5 may if required also be of multipart construction, particularly with a separately formed deformation region 5A.

In the second embodiment, the cover 5 is at least substantially plug-like at least in the region of the recess 7A or the deformation region 5A. However, other configurations are also possible.

The device 1 may, if required, also comprise a plurality of conveying devices 7. These may have separate deformation regions 5A which can in particular be actuated independently of one another. The different deformation regions 5A may selectively be formed by one common piece of material or by separate pieces of material or components.

If the device 1 or conveying device 7 comprises a plurality of deformation regions 5A, these may, if necessary, also be actuated by means of a joint actuating device jointly and/or controlled to be actuated at staggered times. In this way a positive pressure and/or negative pressure can be produced as desired. The different deformation regions 5A can then perform different functions in the device 1 or in the fluidic system 4 through different channels, for example.

The present invention or device 1 or conveying device 7 forms, in particular, a pump that is, particularly preferably, manually actuatable.

The conveying device 7 or the deformation region 5A may if required assume both the non-deformed and the deformed position as a stable position, in each case, the transition between them requiring a certain resistance to be overcome, for example in the manner of a so-called "clicker".

As already mentioned, the present invention and device 1 may be used for different samples 2, such as blood, urine, sputum, cell culture and fermentation media, waste water or the like, particularly for the retention or filtration of eukaryotic and prokaryotic cells, cell compositions, protein and lipid aggregates or the like.

In particular, the present invention and device 1 permit the filtration of microparticles, including so-called beads, which have a reagent bound to their surface, which have an affinity for molecules from the sample 2 and are used by binding in order to concentrate target molecules (analyte, biomarkers or the like) contained in the sample 2.

Moreover, the present invention and device 1 may be used to remove molecules present in the sample 2 (e.g. proteins, nucleic acids) or particles (e.g. viruses) and/or for purification, for example by adsorptive binding.

Furthermore, the present invention and device 1 may be used for example by means of indicators (dyes) the presence or absence of a target molecule and/or particles or the like which may or may not be present in the sample 2.

LIST OF REFERENCE NUMERALS 1 device
2 sample
3 support
3A first support region
3B second support region
3C weakened breaking point
4 fluidic system
4A receiving channel
4B reservoir
4C connecting channel
4D discharge channel
5 cover
5A deformation region 5B fixing region
5C connecting region
5D deflecting region
6 separating device
6A filter element
6B filter element
6C filter element
6D housing
6E depressing device
6F cover
6G aerating opening
6H stop element
7 conveying device
7A recess
7B venting device
7C vent opening
7D valve
7E aerating channel
7F transitional region
7G ram
7H actuating element

The invention claimed is:

1. A device (1) for the manipulation of a liquid sample (2), comprising:
 a support (3) which forms a fluidic system (4), a separating device (6) for the sample (2), which is arranged on a first region (3A) of the support (3),
 a reservoir (4B) disposed in a second region (3B) of the support,
 a receiving channel (4A) disposed between the first region (3A) and the reservoir (4B),
 a conveying device (7) configured to generate both negative pressure and positive pressure for conveying the liquid sample (2), where the conveying device (7) is arranged on the second region (3B) of the support (3), separate from the separating device (6), or is integrated therein, at least one vent channel (7E) having a first end in fluid communication with the conveying device (7), extending from the conveying device (7) and adjacent to the receiving channel (4A), and having a second end terminating in region between the first and second regions of the support (3);
 a separating mechanism (3C) configured to separate the first region (3A) from the second region (3B) and to sever the receiving channel (4A) and the vent channel (7E) therebetween, wherein:
 prior to the separating mechanism (3C) separating the first region (3A) from the second region (3B), the conveying device (7) is configured to generate negative pressure to at least assist in drawing the liquid sample (2) from the first region (3A) of the support (3), through the receiving channel (4A) and into the reservoir (4B) and the first end of the vent channel (7E) that is in fluid communication with the conveying device (7) does not influence the negative pressure therein as the second end of the vent channel (7E) is terminated and is not in fluid communication with an exterior of the fluidic system (4),
 after the separating mechanism (3C) separates the first region (3A) from the second region (3B) and severs the vent channel (7E) therebetween, the first end of the vent channel (7E) is configured to prevents any residual influence of the negative pressure in the conveying device, as a result of a severed end of the vent channel (7E) being in fluid communication with an exterior of the fluidic system (4), and
 after the separating mechanism (3C) separates the first region (3A) from the second region (3B) and severs the receiving channel (4A) therebetween, the conveying device (7) is configured to generate positive pressure to at least assist in forcing the liquid sample (2) from the reservoir (4B) and out of the device (1) through the receiving channel (4A).

2. A device for the manipulation of a liquid sample (2) according to claim 1, wherein the conveying device (7) comprises a deformation region (5A) of the cover (5), the deformation region (5A) being in particular elastically deformable so as to generate the negative pressure and the positive pressure.

3. The device according to claim 2, wherein the cover (5) or the deformation region (5A) is embodied to be at least substantially flat, planar or film-shaped or a combination thereof.

4. The device according to claim 2, wherein the cover (5) covers a flat side of the support (3) at least substantially completely.

5. The device according to claim 2, wherein after deformation the cover (5) or the deformation region (5A) generates the negative pressure or conveys the sample (2) by elastic restoration.

6. The device according to claim 2, wherein the deformation region (5A) can be pressed in manually, while a valve (7D) closes so as to generate the negative pressure during the preferably elastic restoration of the deformation region (5A).

7. The device according to claim 2, wherein the cover (5) or the deformation region (5A) covers a flat or dish-shaped depression or recess (7A) in the support (3).

8. The device according to claim 2, wherein the cover (5) or the deformation region (5A) is of a plug-like configuration.

9. The device according to claim 2, wherein the conveying device (7) or the deformation region (5A) forms or comprises a ram (7G).

10. The device according to claim 2, wherein the cover (5) is formed in one piece with the deformation region (5A).

11. The device according to claim 2, wherein the separating device (6) operates to filter the sample (2), and the filtration may be accelerated or assisted by the positive pressure or negative pressure produced.

12. The device according to claims- 1, wherein the separating device (6) can be separated off after the filtration, particularly by separating off a region (3A) of the support (3).

* * * * *